United States Patent [19]

Pasternak et al.

[11] Patent Number: 4,952,318

[45] Date of Patent: Aug. 28, 1990

[54] SEPARATIONS OF OXYGENATES

[75] Inventors: Mordechai Pasternak, Spring Valley; Tansukhlal G. Dorawala, Wappingers Falls, both of N.Y.

[73] Assignee: Texaco Inc., White Plains, N.Y.

[21] Appl. No.: 141,449

[22] Filed: Jan. 7, 1988

[51] Int. Cl.$^5$ ............................................. B01D 13/00
[52] U.S. Cl. ........................... 210/638; 159/DIG. 28; 203/17; 203/18; 210/640; 210/641
[58] Field of Search ........... 210/638, 640, 641, 500.27, 210/500.36; 159/DIG. 28; 203/14, 18, 17

[56] References Cited

U.S. PATENT DOCUMENTS 2,956,070 10/1960 Jennings et al. .................... 210/640
4,728,429 3/1988 Cabasso et al. ..................... 210/638

*Primary Examiner*—Ivars Cintins
*Attorney, Agent, or Firm*—Robert A. Kulason; James J. O'Loughlin; Carl G. Seutter

[57] ABSTRACT

A dilute solution of methyl ethyl ketone is concentrated by pervaporation through a fluorinated ion exchange membrane which has been exchanged with a quaternary ammonium cation.

13 Claims, No Drawings

SEPARATIONS OF OXYGENATES

FIELD OF THE INVENTION

This invention relates to the separation of oxygenates. More particularly it relates to a process for recovery of oxygenates such as alcohols, ketones, and aldehydes from aqueous compositions.

BACKGROUND OF THE INVENTION

As is well known to those skilled in the art, it is possible to remove water from mixtures thereof with organic liquids by various techniques including adsorption or distillation. These conventional processes, particularly distillation, are however characterized by high capital cost. In the case of distillation for example the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. When the material forms an azeotrope with water, additional problems may be present which for example, could require that separation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the vapor pressure of the permeating species.

Illustrative membranes which have been employed in prior art techniques include those set forth in the following table:

TABLE

| Separating Layer | References |
| --- | --- |
| Nafion brand of perfluorosulfonic acid | Cabasso and Liu J. Memb. Sci. 24, 101 (1985) |
| Sulfonated polyethylene | Cabasso, Korngold & Liu J. Pol. Sci: Letters, 23, 57 (1985) |
| Fluorinated Polyether or Carboxylic Acid fluorides | U.S. Pat. No. 4,526,948 to Dupont as assignee of Resnickto |

It is an object of this invention to provide a novel membrane characterized by its ability to effect separation of water from oxygenates such as methyl ethyl ketone. Other objects .will be apparent to those skilled in the art.

STATEMENT OF THE INVENTION

In accordance with certain of its aspects, this invention is directed to a method which comprises passing a charge aqueous dilute solution of an organic oxygen-containing component which is at least slightly soluble in water into contact with, as a pervaporation membrane, a high molecular weight ion exchange resin in membrane form having carbon atoms in the backbone bearing a pendant acid group which membrane has been contacted with a quaternary ammonium salt containing hydrocarbyl groups each of which contains at least four carbon atoms;

maintaining a pressure drop across said pervaporation membrane thereby forming a retentate containing decreased content of organic oxygen-containing component and a permeate containing increased content of organic oxygen-containing component; and recovering said permeate containing increased content of organic oxygen-containing component.

In accordance with certain of its other aspects, this invention is directed to a non-porous membrane comprising a high molecular weight non-porous resin in membrane form bearing a pendant acid group, the surface of said membrane having been contacted with a quaternary ammonium salt containing hydrocarbyl groups each of which contains at least four carbon atoms.

DESCRIPTION OF THE INVENTION

The Charge Solution

The charge aqueous solution of organic oxygen-containing component which may be treated by the process of this invention may include oxygen-containing compounds such as alcohols, glycols, polyols, aldehydes, ketones, etc. When the oxygen-containing component is an alcohol, it may be for example ethanol, propanol, isopropanol, n-butanol, isobutanol, t-butanol, hexanols, octanols, etc. When the oxygen-containing component is a glycol it may be for example ethylene glycol, propylene glycol, butylene glycol, etc. When the oxygen-containing component is a polyol, it may be for example glycerine, sorbitol, pentaerythritol, trimethylolmethane, polyoxethylene (or propylene) polyol, etc. When the oxygen-containing component is an aldehyde, it may for example be formaldehyde, acetaldehyde, etc. When the oxygen-containing component is a ketone, it may for example be acetone, methyl ethyl ketone, acetophenone, etc.

Although it may be possible to separate oxygen-containing components which are infinitely miscible with water—such as ethanol, acetone, etc., the advantages of this invention may be more readily apparent when the oxygen-containing component is of limited miscibility with water. Typical of such compounds is methyl ethyl ketone which is soluble in water at 25° C. to the extent of 30 parts per 100 parts of water. Water is soluble in methyl ethyl ketone at 25° C. to the extent of 12 parts per 100 parts of ketone. Normal butanol is soluble in water to the extent of 12 parts in 100 parts of water at 25° C.; and water is soluble in n-butanol at 25° C. to the extent of 19 parts per 100 parts of n-butanol.

In one of its aspects, this invention may be directed to a process for treating an aqueous solution of a component which is infinitely miscible with water to form product which contains less water.

In a more preferred embodiment, the invention may be directed to a process for treating an aqueous solution of a component which is only slightly soluble in water; and in this embodiment, the process may be carried out to yield either a single phase permeate solution containing increased concentration of one component or, alternatively if the process is carried out e.g. for a longer period, a two phase permeate The advantages of this invention in certain of its aspects are particularly apparent when the charge aqueous dilute solution is a homogeneous solution containing a component which is less than infinitely miscible with water and the concentration of oxygen-containing component is below the point at which a two-phase system is formed—and the first pervaporation step across the membrane is carried out to yield a concentration of oxygen-containing component which is at least as great as the concentration at which a two-phase mixture is formed.

In the preferred embodiment, the first pervaporation step may be carried out to yield permeate in which the concentration of oxygen-containing component is greater than the solubility thereof in water whereby a two phase system is obtained.

Illustrative charge solutions which may be employed in practice of this invention may include:

(i)

2 w % methyl ethyl ketone
98 w % water (ii)

10 w % methyl ethyl ketone
90 w % water (iii)

1.5 w % n-butanol
98.5 w % water (iv)

5 w % n-butanol
95 w % water (v)

9.9 w % isopropanol
90.1 w % water (vi)

0.9 w % ethanol
99.1 w % water

THE MEMBRANE

The first pervaporation membrane which may be utilized in practice of the process of this invention may be a high molecular weight resin in membrane form. The membrane may be formed of a non-porous material such as polyolefin (e.g. polyethylene, polypropylene, polystyrene, copolymers of ethylene-propylene, terpolymers of ethylene-propylene-third monomer such as 1,4-hexadiene or dichloropentadiene or ethylidene norbornene); vinyls such as polyvinyl chloride, polyvinyl acetate, etc. Clearly the molecular weight of the membrane may vary depending on the species. The thickness of the membrane may typically be 130-430 microns, say about 190 microns.

The ion exchange resins which may be employed in membrane form are characterized by the presence of a pendant acid group such as a —COOH group or more preferably a —SO$_3$H group, or both. These pendant groups containing counter ions may be introduced into the resin in known manner, if not already present therein, by functionalization with appropriate reagents.

The first membrane preferentially retains water and passes non-aqueous media.

A preferred class of membranes may include those which are perfluorinated (i.e. contain substantially no hydrogen atoms other than those on the pendant acid e.g.—SO$_3$H groups). These membranes may typically contain, the structure

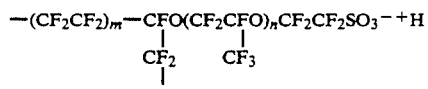

One acid resin membrane which is particularly preferred is that first set forth in the following table which lists commercially available ion exchange resin membranes which may be employed:

TABLE

A. The Nafion-H 117 brand of perfluorinated resin membrane made by DuPont characterized by a thickness of 190 microns having the structure

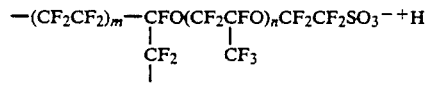

B. The Nafion 901 brand of perfluorinated resin membrane (of thickness about 190 microns) which is characterized by the same general formula as A above except that it also contains —COOH groups in addition to —SO$_3$H groups.

C. Sulfonated polyethylene

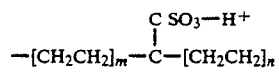

TREATMENT OF THE MEMBRANE

Treatment of the first membranes to render them useful in the process of the instant invention includes contacting at least the surface which is to contact the charge aqueous dilute solution with a quaternary ammonium salt containing four hydrocarbyl groups each of which contains at least four carbon atoms. Although both sides of the membrane may be so treated, no advantage is believed to be thereby obtained. Both sides may normally be treated as a matter of convenience in operation.

The quaternary ammonium salt may be characterized by the formula R$_4$NX.

In the above formula, R may be hydrocarbon selected from the group consisting of alkyl, aralkyl, cycloalkyl aryl, and alkaryl including such radicals when inertly substituted. When R is alkyl, it may be typically be n-butyl, i-butyl, sec-butyl, amyl, octyl, decyl, octadecyl, etc. When R is aralkyl, it may typically be benzyl, beta-phenylethyl, etc. When R is cycloalkyl, it may typically be cyclohexyl, cycloheptyl, cyclooctyl, 2-methylcycloheptyl, 3-butylcyclohexyl, 3-methylcyclohexyl, etc. When R is aryl, it may typically be phenyl, napthyl, etc.

When R is alkaryl, it may typically be tolyl, xylyl, etc. R may be inertly substituted i.e. it may bear a non-reactive substituent such as alkyl, aryl, cycloalkyl, ether, etc. Typically inertly substituted R groups may include 2-ethoxybutyl, carboethoxybutyl, 4-methyl cyclohexyl, p-chlorophenyl, etc. The preferred R groups may be lower alkyl, i.e. $C_4$–$C_8$ alkyl, groups including e.g. butyls, amyls, hexyls, octyls, etc. R may preferably be n-octyl.

The R groups may be different, although preferably they will be the same. X is an anion typically a halide, preferably chloride or bromide—most preferably bromide. Typical quaternary ammonium salts which may be employed (the first listed being preferred) may include:

TABLE tetraoctyl ammonium bromide
tetraheptyl ammonium bromide
tetrahexyl ammonium bromide
tetrapentyl ammonium bromide
tetrabutyl ammonium bromide
tetrabutyl ammonium fluoride
methyl, trioctyl ammonium bromide etc.

In practice of the invention, the first acid membrane may be treated with the quaternary ammonium halide. The latter may be employed as a 5 w %–50 w %, say, 110 w % solution (corresponding to about 0.2M) in solvent, typically an alcohol such as isopropyl alcohol. Contact may be at 20° C.–40° C., say 25° C. for 12–48 hours, say 24 hours with mild agitation. Thereafter, the treated membrane may be washed 2–5, say 3 times for 10–50 minutes, say 30 minutes at 20° C.–40° C., say 25° C. with isopropanol alcohol followed by washes with a 50/50 mixture of isopropanol and water and drying at 20° C.–40° C., say 35° C. for 5–20 minutes, say 10 minutes.

The membranes of this invention may be utilized in various configurations. It is, for example, possible to utilize the membrane in a plate-and-frame configuration in which the separating membrane layer may be mounted on a porous support layer.

In one preferred embodiment, it is possible to utilize the system of this invention as a tubular or hollow fibre. In this embodiment, the resin membrane may be extruded as a fine tube with a wall thickness of typically 0.001–0.1 mm. The extruded tubes are passed through a bath of quaternary ammonium salt in solvent. A bundle of these tubes is secured (with an epoxy adhesive) at each end in a header; and the fibres are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating membrane and permeate is collected in the shell side.

PERVAPORATION

It is a feature of the membrane of this invention that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 1 mm. Hg. The pressure on the permeate side of the membrane is below the partial pressure of the permeate.

For general background on pervaporation, note U.S. Pat. Nos. 4,277,344; 4,039,440; 3,926,798; 3,950,247; 4,035,291; etc.

It is a feature of this invention that the novel membrane may be particularly useful in pervaporation processes for treating aqueous solutions of organic oxygen-containing components typified by methyl ethyl ketone.

A typical charge may be a 2–10 w % say 10 w % aqueous solution of methyl ethyl ketone.

In practice of the pervaporation process of this invention, the charge aqueous solution at 40° C.–80° C., say 70° C. may be passed into contact with the non-porous membrane of this invention. A pressure drop of about one atmosphere is commonly maintained across the membrane. Typically, the feed or charge side of the membrane is at about atmospheric pressure and the permeate or discharge side of the membrane is at a pressure of about 0.5–50, preferably 5–20, say 1 mm.Hg.

The permeate which passes through the membrane includes the oxygen-containing component and a small proportion of the water from the charge liquid. Typically, the retentate contains 90–99.9, say 99 w %–100 w % water. Permeate is recovered in vapor phase.

Pervaporation may typically be carried out at a flux of 0.1–10, say 0.50 gallons per square foot per day (gfd) which corresponds to about 0.17–16.9, say 0.68 kilograms per square meter per hour (kmh). Typically, the units may have a selectivity (measured in terms of w % oxygen-containing component in the permeate during pervaporation at 25°–70° C. of a 5–10% aqueous solution of methyl ethyl ketone through a standard membrane of 0.19 mm i.e. 190 microns thickness) of up to 80%, say 78% methyl ethyl ketone.

It will be apparent to those skilled in the art that the degree of concentration of oxygen-containing component in the permeate may be a function of several variables. Among these may be the composition of the membrane and the counter ion treating agent $R_4NX$, the temperature and pressure of pervaporation, the effective time of contact between the charge solution and the membrane or, alternatively expressed, the area of contact with the membrane.

For example it may be desirable in one embodiment to effect only a small increase in concentration of a soluble component or alternatively it may be desirable to augment the concentration to a point above which it is possible to obtain a two-phase permeate.

THE SEGREGATION STEP

When the pervaporation utilizing the quaternary counter ion membrane is carried out, as in the preferred embodiment, to yield a two-phase liquid system, the phases are preferably passed to a phase segregation step wherein they are separated.

This may occur in a quiescent settling zone, in a centrifuge, etc. Operation is typically carried out at atmospheric pressure at 0° C.–50° C., say, 10° C. and commonly at a temperature which is the same as the effluent temperature of the permeate from the pervaporation operation.

In the case of the preferred embodiment wherein a 10 w % aqueous solution of methyl ethyl ketone has been separated by pervaporation through an ion exchange membrane, the permeate may typically contain 23–80 w %, say 78 w % methyl ethyl ketone in a two-phase mixture at 0° C.–50° C., say 10° C.

Segregation may yield a supernatant or lighter layer containing augmented concentration of oxygen-containing component in water and a lower or heavier layer containing a diminished concentration of oxygen-containing component. In the case of the preferred methyl ethyl ketone system wherein 100 parts of the feed of increased concentration to the segregation operation is at 25° C.–50° C., say 10° C. and is a two-phase mixture containing overall 23 w %–80 w %, say 78 w % methyl ethyl ketone, the segregation operation may yield 5–72 parts, say 72 parts of single phase lighter augmented layer typically containing say 89 w % of methyl ethyl ketone and say 11 w % water. Also withdrawn from the segregation operation may be 13–19 parts, say 19 parts of a single phase heavier diminished layer typically containing say 23 w % methyl ethyl ketone and say 77 w.% water. This latter diminished phase may be recycled to the charge to the segregation pervaporation operation.

In practice of the process of this invention, according to certain of its aspects, the augmented layer from phase segregation may be passed to a second pervaporation operation.

SECOND PERVAPORATION

The second pervaporation step of this invention may be carried out in manner comparable to and utilizing conditions generally utilized in the first pervaporation operation—except of course that the membrane is different.

These hydrophilic membranes employed in the second pervaporation step preferably pass water and retain non-aqueous media.

The separating layer may include a non-porous film of cross-linked polyvinyl alcohol of thickness of about 1–10 microns preferably 1–5 microns, say 1.5 microns. The layer is formed from polyvinyl alcohol which has been prepared by hydrolysis of polyvinyl acetate-typically 50–100% hydrolyzed, preferably 90–100%, say 100% hydrolyzed. The charge polyvinyl alcohol has a molecular weight of 20,000–200,000 say 115,000. Typically it may be employed as a 5–10 w %, say 7 w % aqueous solution. A commercially available product which may be employed is the Aldrich brand of 100% hydrolyzed polyvinyl alcohol of molecular weight of about 115,000 as a 7 w % aqueous solution.

The membrane or sheet of cross-linked polyvinyl alcohol separating layer is formed in situ on the porous support layer. This is effected by use, as a cross linking agent, of an aliphatic dialdehyde containing at least three carbon atoms. Preferably the aliphatic dialdehyde may contain 3–8 carbon atoms, most preferably 5 carbon atoms. Typical alphatic dialdehydes which may be employed may include:

TABLE glutaraldehyde
2-hydroxyhexanedial - 1,6
malonic dialdehyde
succinic dialdehyde
hexanedial - 1,6

The preferred alphatic dialdehyde is glutaraldehyde. Aldehydes falling outside the scope of this invention typified by formaldehyde, glyoxal, or succinic semi aldehyde yield membranes which are characterized by unsatisfactory performance. Performance is judged by the ability of a membrane system to give a permeate containing less than 1 w % ethylene glycol (from a charge containing 85 w % ethylene glycol and 15 w % water) with a flux of at least 0.5 kilograms/meter$^2$/hour (kmh) at a feed temperature of 80° C. and with a permeate pressure of 5 mmHg and a condenser cooled by liquid nitrogen). Compositions falling outside the scope of this invention may be characterized by unsatisfactory selectivity or unsatisfactory productivity or both.

In situ crosslinking may be carried out by casting 5–10 w %, say 7 w % aqueous solution of polyvinyl alcohol which contains the aliphatic dialdehyde crosslinking agent. The mole ratio of crosslinking agent to polyvinyl alcohol may be 0.05–0.30, say 0.2.

Crosslinking is carried out, in the presence of acid catalyst, preferably inorganic acid. Sulfuric acid is preferred. Hydrochloric acid is much less preferred—because it yields membranes of poor selectivity, although the flux may be high.

It may be possible in one embodiment to crosslink the polyvinyl alcohol separating layer in one step by adding to the aqueous solution of polyvinyl alcohol and dialdehyde, the acid catalyst, preferably sulfuric acid, in mole ratio of acid to dialdehyde of 0.08–0.14, say 0.1.

In another embodiment, it may be possible to apply to the porous support layer, an aqueous invention of polyvinyl alcohol and dialdehyde. This may be dried at 40° C. –80° C., say 50° C. for 2–10 minutes, say 4 minutes to form a film. There may then be added onto the surface of this film a viscous solution containing 2–7 w %, say 3.5 w % of polyvinyl alcohol and having a mole ratio of sulfuric acid to dialdehyde of 0.08–0.14, preferably 0.1.

The composite membrane, whether prepared by the one-step or the two-step process may then be cured in an oven at 100°–200° C., say 125° C. for 1–30 minutes, say 2 minutes to yield a polyvinyl alcohol film having a thickness of 1–10 microns, say 3 microns.

The composite membrane may comprise (i) an optional carrier layer, characterized by porosity and mechanical strength, for supporting a porous support layer and a separating layer, (ii) a polysulfone porous support layer of molecular weight of 5,000–100,000, of thickness of 10–80 microns, and of molecular weight $\overline{M}_n$ cut off of 25,000–100,000 and (iii) as a non-porous separating layer polyvinyl alcohol of molecular weight of 20,000–200,000 which has been crosslinked with an aliphatic dialdehyde containing 3–8 carbon atoms.

When the composite membrane is used with a charge containing a ketone such as acetone or methyl ethyl ketone, it is preferred to utilize a support layer (such as a polyacrylonitrile which is inert to these components; (the polysulfone is attacked by certain ketones such as acetone or methyl ethyl ketone).

Typical second membranes which may be employed may be those listed in the following table, the first listed being preferred.

TABLE

A. A porous non-woven polyester backing as carrier layer bearing as porous support layer a microporous support layer of polysulfone of molecular weight cutoff of 20,000 bearing a separating layer of polyvinyl alcohol ($M_n$ 115,000) which has been cross-linked with glutaraldehyde.

B. A membrane as in A above but including as the support layer a matrix of polyacrylonitrile.

In practice of the second pervaporation step in accordance with certain aspects of the process of the invention, the liquid of augmented concentration of oxygen-containing component may be passed into contact with the second pervaporation membrane in manner generally comparable to that utilized during the first pervaporation. Typical temperature of operation may be 70° C.-90° C., say 70° C.

Permeate of reduced content of organic oxygen containing component may typically contain 0-1 w %, say about 0.5% of oxygen-containing component. Retentate of enriched content of organic oxygen-containing component may typically contain 90-99 w %, say about 99 w % of organic oxygen-containing component.

DESCRIPTION OF SPECIFIC EMBODIMENT

Practice of the process of this invention will be apparent to those skilled in the art from the following wherein, as elsewhere in this specification, all parts are parts by weight unless otherwise specified.

EXAMPLE I

In this example which represents the best mode presently known of carrying out the first step of the process of this invention according to certain of its aspects, the charge aqueous dilute solution of organic oxygen-containing component may be a 10 w % single phase solution of methyl ethyl ketone in water at 70° C.

The ion exchange employed is the Nafion-H 117 brand of perfluorinated resin A of the Table supra which membrane has been treated for 24 hours at 25° C. with a 0.2M solution in isopropyl alcohol of tetra n-octyl ammonium bromide by immersion (to contact both sides) followed by three similar washing steps. The first washing is carried out by immersion for 0.5 hours at 25° C. in isopropanol. The second and third washings are carried out similarly in isopropanol/water.

The membrane may be mounted in a pervaporation cell having a total surface area of 46 square centimeters.

Charge methyl ethyl ketone, 10 w % in water, is subjected (100 parts) to first pervaporation at 70° C. The retentate, is substantially pure water. The permeate is of increased organic content.

The permeate contains 78.27 w % methyl ethyl ketone and this separates into two phases. The methyl ethyl ketone phase is 84.6 w % of total permeate. This corresponds to a separation factor of 30.09 and a flux (in gallons per square foot per day) of 0.2.

The Separation Factor S which represents the ability of the membrane to recover oxygenate is calculated as follows:

$$S = \frac{\left(\frac{X_n}{X_m}\right)_p}{\left(\frac{X_n}{X_m}\right)_F}$$

wherein $X_n$ and $X_m$ are the weight fractions of oxygen-containing component and water respectively in the permeate (p) and the feed (F). A system showing no separation at all would have a Separation Factor of 1: and a system showing perfect 100% separation would have a Separation Factor of infinity.

EXAMPLE II

In this example which shows further handling of the permeate of increased content of oxygen-containing component recovered in Example I, that permeate is passed to a settling tank in which the segregation operation is carried out. After 5 hours at 25° C., a lower aqueous phase of diminished methyl ethyl ketone content (containing a 23 w % aqueous solution of methyl ethyl ketone) is drawn off and recycled to be mixed with the charge to the first pervaporation operation.

The augmented upper layer from the segregation operation is withdrawn at 25° C. as an 87 w % methyl ethyl ketone solution in water and passed to the second pervaporation operation.

Second pervaporation is carried out using a selective separating layer which is mounted on a commercially available composite containing a non-woven polyester backing as carrier layer bearing, as a porous support layer, a microporous membrane polyacrylonitrile layer of molecular weight cut-off of 20,000. The selective separating hydrophilic membrane is formed in situ by a one-step coating process. The separating layer is formed from a solution containing 10 g of 7 w % polyvinyl alcohol (M.W. of 115,000) in water to which was added 1.37 g of a 25 w % aqueous solution of glutaraldehyde and 0.15 g of 0.5N sulfuric acid solution. This mixture was stirred until homogeneous and spread onto the polyacrylonitrile microporous support to form a membrane film 4 mils thick. The assembly was cured in an oven for 15 minutes at 150° C.

Pervaporation utilizing this hydrophilic membrane (carried out at 80° C. in manner generally similar to the first pervaporation) yields a permeate of reduced content of oxygen-containing composition and a retentate of enriched content of methyl ethyl ketone.

EXAMPLE III

This Example illustrates that it is possible to utilize the membrane of this invention to concentrate a single phase composition to yield a more concentrated single phase composition.

A single phase solution of 10.3 w % isopropanol in water at 70° C. is subjected to first pervaporization utilizing the same membrane and conditions as set forth in Example I.

The single phase permeate contains 33.8 w % isopropanol. This represents a Separation Factor of 4.34 at a flux of 0.02 gfd.

EXAMPLE IV-XVIII

In this series of Examples, the charge oxygen-containing solution is a single phase 2 w % solution of methyl ethyl ketone in water. The first membrane is the Nafion-H 117 brand membrane used in Example I except that, as indicated, it is treated with a different quaternary ammonium bromide $R_4NBr$—i.e. the butyl, pentyl, n-hexyl, or n-heptyl analogues of the n-octyl. The tetraalkyl ammonium bromides are employed in manner similar to that used with the tetra n-octyl ammonium bromide of Example I.

Examples IV-VIII utilize a temperature of 25° C., Examples IX-XIII 50° C. and Examples XIV-XVIII 70° C.

There are recorded "Permeate (% MEK)" which indicates the percentage of MEK in the total permeate, whether the permeate is single phase or two-phase, the Separation Factor, and the flux in gfd-gallons per square foot per day.

An asterisk next to the Permeate value indicates that the Permeate contains two-phases. All other Permeates are single phase.

TABLE

Selective Removal of MEK from 2% MEK/Water Feed Nafion-NR4 Membranes in Pervaporation at Various Temperatures

| Example | Membrane | Permeate (% MEK) | Separation Factor | Flux$^2$ (gfd) |
|---|---|---|---|---|
| IV | Nafion-N(Octyl)4 | 5.60 | 2.91 | 0.001 |
| V | Nafion-N(Heptyl)4 | 10.67 | 5.85 | 0.009 |
| VI | Nafion-N(Hexyl)4 | 3.54 | 1.80 | 0.004 |
| VII | Nafion-N(Pentyl)4 | 1.49 | 0.74 | 0.07 |
| VIII | Nafion-N(Butyl)4 | 2.30 | 1.15 | 0.12 |
| IX | Nafion-N(Octyl)4 | 22.85* | 14.51 | 0.007 |
| X | Nafion-N(Heptyl)4 | 15.08 | 8.70 | 0.05 |
| XI | Nafion-N(Hexyl)4 | 12.49 | 6.99 | 0.02 |
| XII | Nafion-N(Pentyl)4 | 3.59 | 1.82 | 0.13 |
| XIII | Nafion-N(Butyl)4 | 2.16 | 1.08 | 0.22 |
| XIV | Nafion-N(Octyl)4 | 24.91* | 16.01 | 0.02 |
| XV | Nafion-N(Heptyl)4 | 14.31 | 8.06 | 0.14 |
| XVI | Nafion-N(Hexyl)4 | 15.67 | 8.97 | 0.06 |
| XVII | Nafion-N(Pentyl)4 | 4.90 | 2.49 | 0.27 |
| XVIII | Nafion-N(Butyl)4 | 3.03 | 1.57 | 0.40 |

MEK is an abbreviation for methyl ethyl ketone.

The following inter alia may be noted from the above table:

(i) practice of the instant invention permits enrichment of a charge stream containing 2 w % methyl ethyl ketone;

(ii) generally as the length of the substituent on the quaternary ammonium compound is increased (over the range of C4 to C8), the amount of MEK in the permeate increases, the Separation Factor increases, and the Flux decreases—although there are exceptions;

(iii) except in the case of Examples IX and XIV, all the permeates are single phase; and (iv) best results appear to be attained at higher temperature—the best result, in terms of Separation Factor being achieved at 70° C.

EXAMPLES XIX-XXXIII

In this series of Examples, the pattern of Examples IV-XVIII is followed except that the charge is a 5 w % aqueous solution of MEK. Examples XIX-XXIII are carried out at 25° C., Examples XXIV-XXVIII at 50° C. and Examples XXIX-XXXIII at 75° C.

TABLE

Selective Removal of MEK from 5% MEK/Water Feed Nafion-NR4 Membranes in Pervaporation at Various Temperatures

| Example | Membrane | Permeate (% MEK) | Separation Factor | Flux$^2$ (gfd) |
|---|---|---|---|---|
| XIX | Nafion-N(Octyl)4 | 14.08 | 2.95 | 0.002 |
| XX | Nafion-N(Heptyl)4 | 25.40* | 6.12 | 0.02 |
| XXI | Nafion-N(Hexyl)4 | 4.37 | 0.82 | 0.01 |
| XXII | Nafion-N(Pentyl)4 | 6.37 | 1.22 | 0.04 |
| XXIII | Nafion-N(Butyl)4 | 5.10 | 0.97 | 0.10 |
| XXIV | Nafion-N(Octyl)4 | 25.81* | 7.13 | 0.02 |
| XXV | Nafion-N(Heptyl)4 | 27.28* | 7.69 | 0.09 |
| XXVI | Nafion-N(Hexyl)4 | 26.52* | 7.40 | 0.04 |
| XXVII | Nafion-N(Pentyl)4 | 11.45 | 2.65 | 0.15 |
| XXVIII | Nafion-N(Butyl)4 | 6.79 | 1.49 | 0.24 |
| XXIX | Nafion-N(Octyl)4 | 42.14* | 13.14 | 0.04 |
| XXX | Nafion-N(Heptyl)4 | 24.87* | 5.97 | 0.22 |
| XXXI | Nafion-N(Hexyl)4 | 25.94* | 6.32 | 0.10 |
| XXXII | Nafion-N(Pentyl)4 | 14.28 | 3.01 | 0.30 |
| XXXIII | Nafion-N(Butyl)4 | 8.50 | 1.68 | 0.43 |

*Two phases of MEK and water were formed.

From the above Table, conclusions may be drawn comparable to those noted for Examples IV-XVIII.

EXAMPLES XXXIV-XLVIII

In this series of Examples, the pattern of Examples IV-XVIII is followed except that the charge is a 10 w % aqueous solution of MEK. Examples XXXIV-XXXVIII are carried out at 25° C., Examples XXXIX-XLIII at 50° C., and Examples XLIV-XLVIII at 70° C. In all cases (except Examples XXXVIII and XLIII) two phases are observed in the permeate. There is also tablulated the amount of upper MEK phase as a w % of the total permeate.

TABLE

Selective Removal of MEK from 10% MEK/Water Feed Nafion-NR4 Membranes in Pervaporation at Various Temperatures

| Example | Membrane | MEK Phase (% in Permeate) | Permeate (% MEK) | Separation Factor | Flux (gfd) |
|---|---|---|---|---|---|
| XXXIV | Nafion-N(Octyl)4 | 87.27 | 80.0 | 37.24 | 0.02 |
| XXXV | Nafion-N(Heptyl)4 | 53.38 | 59.4 | 13,62 | 0.04 |
| XXXVI | Nafion-N(Hexyl)4 | 42.86 | 52.38 | 10.24 | 0.02 |
| XXXVII | Nafion-N(Pentyl)4 | 5.06 | 26.34 | 3.33 | 0.08 |
| XXXVIII | Nafion-N(Butyl)4 |  | 16.99 | 1.91 | 0.15 |
| XXXIX | Nafion-N(Octyl)4 | 82.14 | 77.27 | 29.32 | 0.09 |
| XL | Nafion-N(Heptyl)4 | 49.69 | 57.99 | 11.91 | 0.18 |
| XLI | Nafion-N(Hexyl)4 | 53.42 | 59.59 | 12.72 | 0.1 |
| XLII | Nafion-N(Pentyl)4 | 9.09 | 31.21 | 3.91 | 0.23 |
| XLIII | Nafion-N(Butyl)4 |  | 20.71 | 2.25 | 0.37 |
| XLIV | Nafion-N(Octyl)4 | 84.16 | 78.27 | 30.09 | 0.2 |
| XLV | Nafion-N(Heptyl)4 | 67.37 | 68.34 | 18.03 | 0.4 |
| XLVI | Nafion-N(Hexyl)4 | 49.51 | 56.96 | 11.06 | 0.23 |
| XLVII | Nafion-N(Pentyl)4 | 11.11 | 33.34 | 4.18 | 0.45 |
| XLVIII | Nafion-N(Butyl)4 | 0.52 | 23.34 | 2.54 | 0.61 |

EXAMPLES XLIX-LXIII

In this series of Examples, the pattern of Examples IV-XVIII is followed except that the charge is a 1.5 w % solution of n-butanol in water. Examples XLIX-LIII are carried out at 25° C., Examples LIV-LVIII at 50° C. and Examples LIX-LXIII at 70° C.

TABLE

Selective Removal of n-Butanol from 1.5% Butanol/Water Feed Nafion-NR4 Membranes in Pervaporation at Various Temperatures

| Example | Membrane | Permeate (% n-Butanol) | Separation Factor | Flux[2] (gfd) |
|---|---|---|---|---|
| XLIX | Nafion-N(Octyl)4 | 8.41 | 5.58 | 0.002 |
| L | Nafion-N(Heptyl)4 | 5.63 | 3.62 | 0.005 |
| LI | Nafion-N(Hexyl)4 | 0.92 | 0.56 | 0.002 |
| LII | Nafion-N(Pentyl)4 | 0.28 | 0.17 | 0.03 |
| LIII | Nafion-N(Butyl)4 | 0.18 | 0.11 | 0.07 |
| LIV | Nafion-N(Octyl)4 | 10.51 | 7.46 | 0.01 |
| LV | Nafion-N(Heptyl)4 | 9.76 | 6.87 | 0.03 |
| LVI | Nafion-N(Hexyl)4 | 7.45 | 5.11 | 0.02 |
| LVII | Nafion-N(Pentyl)4 | 1.20 | 0.77 | 0.15 |
| LVIII | Nafion-N(Butyl)4 | 0.74 | 0.47 | 0.23 |
| LIX | Nafion-N(Octyl)4 | 13.44* | 9.80 | 0.03 |
| LX | Nafion-N(Heptyl)4 | 10.29 | 7.24 | 0.09 |
| LXI | Nafion-N(Hexyl)4 | 8.25 | 5.67 | 0.05 |
| LXII | Nafion-N(Pentyl)4 | 1.60 | 1.03 | 0.27 |
| LXIII | Nafion-N(Butyl)4 | 1.05 | 0.67 | 0.38 |

*Two phases of n-Butanol and water were formed

It is clear that dilute aqueous solutions of n-butanol may be readily concentrated by use of the membrane of this invention.

EXAMPLES LXIV-LXXVIII

In this series of Examples, the pattern of Examples IV-XVIII is followed except that the charge is a 5 w % solution of n-butanol in water. Examples LXIV-LXVIII are carried out at 25° C., Examples LXIX-LXXIII at 50° C. and Examples LXXIV-LXXVIII at 70° C. Some permeates were two-phase systems.

TABLE

Selective Removal of n-Butanol from 5% Butanol/Water Feed Nafion-NR4 Membranes in Pervaporation at Various Temperatures

| Example | Membrane | Butanol Phase (% of Permeate) | Permeate (% n-Butanol) | Separation Factor | Flux (gfd) |
|---|---|---|---|---|---|
| LXIV | Nafion-N(Octyl)4 | 1.99 | 12.45 | 3.05 | 0.003 |
| LXV | Nafion-N(Heptyl)4 | 0.37 | 11.27 | 2.73 | 0.009 |
| LXVI | Nafion-N(Hexyl)4 | | 10.75 | 2.59 | 0.006 |
| LXVII | Nafion-N(Pentyl)4 | | 2.36 | 0.52 | 0.05 |
| LXVIII | Nafion-N(Butyl)4 | | 1.74 | 0.38 | 0.1 |
| LXIX | Nafion-N(Octyl)4 | 26.31 | 30.22 | 9.52 | 0.02 |
| LXX | Nafion-N(Heptyl)4 | 16.18 | 22.82 | 6.50 | 0.05 |
| LXXI | Nafion-N(Hexyl)4 | 4.24 | 14.10 | 3.61 | 0.03 |
| LXXII | Nafion-N(Pentyl)4 | | 4.80 | 1.11 | 0.17 |
| LXXIII | Nafion-N(Butyl)4 | | 3.25 | 0.74 | 0.25 |
| LXXIV | Nafion-N(Octyl)4 | 33.76 | 35.66 | 12.15 | 0.05 |
| LXXV | Nafion-(Heptyl)4 | 12.17 | 19.89 | 5.45 | 0.14 |
| LXXVI | Nafion-N(Hexyl)4 | 5.33 | 14.89 | 3.84 | 0.09 |
| LXXVII | Nafion-N(Pentyl)4 | | 7.10 | 1.68 | 0.32 |
| LXXVIII | Nafion-N(Butyl)4 | | 5.10 | 1.18 | 0.44 |

Results comparable to Example I may be attained if other first membranes within the scope of this invention are employed.

Results comparable to those attained in Example I may be attained if the charge aqueous solution is as follows:

| Example | Charge Solution |
|---|---|
| LXXIX | 0.9 w % ethanol |
| LXXX | 7 w % glycerine |
| LXXXI | 10 w % sorbitol |
| LXXXII | 5 w % ethylene glycol |
| LXXXIII | 20 w % ethanol |
| LXXXIV | 1 w % acetone |
| LXXXV | 5 w % acetaldehyde |

EXAMPLES LXXXVI-C

In this series of Examples, the pattern of Examples IV-XVIII is followed except that in Examples LXXXVI-XC, the charge is a 1.4 w % aqueous solution of isopropanol, in Examples XCI-XCV, the charge is 5.4 w % isopropanol, and in Examples XCVI-C the charge is 9.9 w % isopropanol—all at 50° C.

The quaternizing agent in Examples, XC, XCV, and C is tetraphenyl phosphorous bromide $(C_6H_5)_3$ P Br.

TABLE

| Example | Membrane | Permeate % IPA | Sep | Flux |
|---|---|---|---|---|
| LXXXVI | Nafion-N(Octyl)4 | 4.91 | 3.64 | 0.004 |
| LXXXVII | Nafion-N(Heptyl)4 | 2.68 | 1.94 | 0.07 |
| LXXXVIII | Nafion-N(Hexyl)4 | 3.44 | 2.51 | 0.002 |
| LXXXIX | Nafion-N(Pentyl)4 | 0.78 | 0.55 | 0.09 |
| XC* | Nafion-P(Phenyl)4 | 0.35 | 0.25 | 0.01 |
| XCI | Nafion-N(Octyl)4 | 12.84 | 2.58 | 0.007 |
| XCII | Nafion-N(Heptyl)4 | 8.28 | 1.58 | 0.007 |
| XCIII | Nafion-N(Hexyl)4 | 9.03 | 1.74 | 0.01 |
| XCIV | Nafion-N(Pentyl)4 | 3.49 | 0.63 | 0.1 |
| XCV* | Nafion-P(Phenyl)4 | 0.54 | 0.1 | 0.01 |
| XCVI | Nafion-N(Octyl)4 | 24.57 | 2.95 | -0.01 |
| XCVII | Nafion-N(Heptyl)4 | 20.12 | 2.28 | 0.01 |
| XCVIII | Nafion-N(Hexyl)4 | 16.71 | 1.82 | 0.01 |
| XCIX | Nafion-N(Pentyl)4 | 7.44 | 0.73 | 0.13 |
| C* | Nafion-P(Phenyl)4 | 0.99 | 0.1 | 0.02 |

From the above Table, it will be seen that generally the quaternary phosphonium is characterized by an undesirably low Flux and Separation Factor. As the number of carbon atoms increases in the alkyl groups, the desired Separation Factor and the concentration of isopropanol in the permeate increase.

EXAMPLES CI-CX

In this series of Examples, the procedure of Examples LXXXVII-C is followed except that the temperature of operation was 70° C. In Examples CI-CIV, the feed concentration is 1.1 w % isopropanol in water. In Examples CV-CVIII the feed concentration is 5.2 w % in water. In Examples CIX-CXII, the feed concentration is 10.3 w % in water.

TABLE

| Example | Membrane | Permeate % IPA | Sep | Flux |
|---|---|---|---|---|
| CI | Nafion-N(Octyl)4 | 5.68 | 5.41 | 0.01 |
| CII | Nafion-N(Heptyl)4 | 4.18 | 3.92 | 0.01 |
| CIII | Nafion-N(Hexyl)4 | 2.98 | 2.89 | 0.01 |
| CIV | Nafion-N(Pentyl)4 | 1.28 | 1.23 | 0.25 |
| CV | Nafion-N(Octyl)4 | 19.11 | 4.32 | 0.01 |
| CVI | Nafion-N(Heptyl)4 | 16.34 | 3.57 | 0.01 |
| CVII | Nafion-N(Hexyl)4 | 10.28 | 2.21 | 0.01 |
| CVIII | Nafion-N(Pentyl)4 | 5.8 | 1.13 | 0.27 |
| CIX | Nafion-N(Octyl)4 | 33.18 | 4.34 | 0.02 |
| CX | Nafion-N(Heptyl)4 | 29.15 | 3.59 | 0.02 |
| CXI | Nafion-N(Hexyl)4 | 23.96 | 2.75 | 0.02 |
| CXII | Nafion-N(Pentyl)4 | 11.57 | 1.14 | 0.26 |

Although this invention has been illustrated by reference to specific embodiments, it will be apparent to those skilled in the art that various changes and modifications may be made which clearly fall within the scope of this invention.

We claim:

1. The method which comprises
passing a charge aqueous dilute solution of an organic oxygen-containing component which is at least slightly soluble in water into contact with, as a pervaporation membrane, a high molecular weight ion exchange resin in membrane form comprising a perfluorinated resin containing carbon atoms in the backbone chain, bearing a pendant acid group which membrane has been contacted with a quaternary ammonium salt containing hydrocarbyl groups each of which contains at least four carbon atoms;
maintaining a pressure drop across said pervaporation membrane thereby forming a retentate containing decreased content of organic oxygen-containing component and a permeate containing increased content of organic oxygen-containing component; and
recovering said permeate containing increased content of organic oxygen-containing component.

2. The method claimed in claim 1 wherein said high molecular weight ion exchange resin in membrane form is a resin containing an —SO3H group as a pendant acid group.

3. The method claimed in claim 1 wherein said high molecular weight ion exchange resin in membrane form is a perfluorinated resin containing the structure

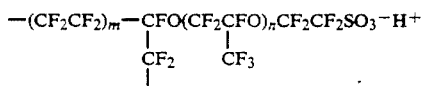

4. The method claimed in claim 1 wherein said quaternary ammonium salt containing hydrocarbyl groups is R4NX wherein R is hydrocarbon, and X is bromide.

5. The method claimed in claim 4 wherein R is an octyl group.

6. The method claimed in claim 5 wherein R4NX is tetra n-octyl ammonium bromide.

7. The method claimed in claim 1 wherein said organic oxygen-containing component which is at least slightly soluble in water is an alcohol or a ketone.

8. The method claimed in claim 1 wherein said organic oxygen-containing component which is at least slightly soluble in water is methyl ethyl ketone.

9. The method claimed in claim 1 which comprises
passing a charge aqueous dilute solution of methyl ethyl ketone into contact with, as a pervaporation membrane, a high molecular weight ion exchange fluorinated resin in membrane form containing the structure

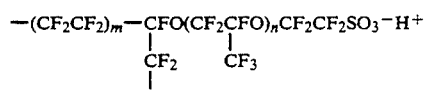

which membrane has been contacted with a quaternary ammonium bromide R4NBr wherein R is an alkyl group containing at least four carbon atoms;
maintaining a pressure drop across said pervaporation membrane thereby forming a retentate containing decreased content of methyl ethyl ketone and a two-phase permeate containing increased content of methyl ethyl ketone; and
recovering said two-phase permeate containing increased content of methyl ethyl ketone.

10. The method claimed in claim 9 including the steps of separating said two-phase permeate thereby forming an organic phase containing augmented content of organic oxygen-containing component and aqueous phase containing diminished content of organic oxygen-containing component;
recovering said organic phase containing augmented content of organic oxygen-containing component.

11. The method claimed in claim 10, including the steps of recovering said aqueous phase containing diminished content of organic oxygen-containing component; and
passing said recovered aqueous phase containing diminished content of organic oxygen-containing component to said charge aqueous dilute solution.

12. The method claimed in claim 10 including the steps of
recovering said organic phase containing augmented content of organic oxygen-containing component;
passing said recovered organic phase containing augmented content of oxygen-containing component into contact with, as a second pervaporation membrane, a high molecular weight second resin in membrane form;
maintaining a pressure drop across said second pervaporation membrane thereby forming a retentate of enriched content of organic oxygen-containing component and a permeate of reduced content of oxygen-containing component; and
recovering said retentate of enriched content of organic oxygen-containing component.

13. The method which comprises
passing a charge aqueous dilute solution of methyl ethyl ketone into contact with, as a pervaporation membrane, a high molecular weight ion exchange fluorinated resin in membrane form containing the structure

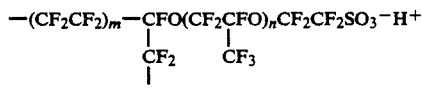

the surface of which membrane has been contacted with a quaternary ammonium bromide $R_4NBr$ wherein R is an alkyl group containing 4-8 carbon atoms;

maintaining a pressure drop across said ion exchange pervaporation membrane thereby forming a retentate containing decreased content of methyl ethyl ketone and a two phase permeate containing increased content of methyl ethyl ketone;

recovering said two-phase permeate containing increased content of methyl ethyl ketone;

separating said two-phase permeate thereby forming an organic phase containing augmented content of methyl ethyl ketone and aqueous phase containing diminished content of methyl ethyl ketone;

recovering said organic phase containing augmented content of methyl ethyl ketone;

passing said recovered organic phase containing augmented content of methyl ethyl ketone into contact with, as a second pervaporation membrane, a high molecular weight second resin in membrane form; and maintaining a pressure drop across said second pervaporation membrane thereby forming a retentate of enriched content of methyl ethyl ketone and a permeate of reduced content of methyl ethyl ketone; and recovering said retentate of enriched content of methyl ethyl ketone.

* * * * *